United States Patent [19]
Sugiyama et al.

[11] Patent Number: 5,660,661
[45] Date of Patent: Aug. 26, 1997

[54] OXYGEN SENSOR

[75] Inventors: Tomio Sugiyama; Masatoshi Suzuki; Hiromi Sano, all of Nagoya; Toshitaka Saito, Toyohashi; Satoru Nomura, Aichi-gun, all of Japan

[73] Assignee: Nippondenso Co., Ltd., Kariya, Japan

[21] Appl. No.: 462,210

[22] Filed: Jun. 5, 1995

Related U.S. Application Data

[62] Division of Ser. No. 226,551, Apr. 12, 1994, Pat. No. 5,447,618.

[30] Foreign Application Priority Data

Apr. 13, 1993 [JP] Japan ................................ 5-110969

[51] Int. Cl.$^6$ ........................................ B32B 9/00
[52] U.S. Cl. ................................. 156/89; 264/618
[58] Field of Search ............................. 428/688, 689, 428/210; 204/426; 429/247; 437/7; 156/89, 90; 264/56, 58, 67

[56] References Cited

U.S. PATENT DOCUMENTS

| | | | |
|---|---|---|---|
| 4,334,974 | 6/1982 | Muller | 204/426 |
| 4,407,057 | 10/1983 | Kimura | 437/7 |
| 4,559,126 | 12/1985 | Mase et al. | |
| 4,940,528 | 7/1990 | Oki et al. | |
| 5,122,487 | 6/1992 | Hayakawa | 204/426 |
| 5,238,549 | 8/1993 | Makino | 204/426 |
| 5,278,007 | 1/1994 | Nanataki | 429/247 |
| 5,447,618 | 9/1995 | Sugiyama | 204/426 |

FOREIGN PATENT DOCUMENTS

| | | |
|---|---|---|
| 61-108957 | 5/1986 | Japan. |
| 61-172054 | 8/1986 | Japan. |
| 2-137777 | 5/1990 | Japan. |

*Primary Examiner*—Patrick Ryan
*Assistant Examiner*—Patrick Jewik
*Attorney, Agent, or Firm*—Cushman, Darby & Cushman IP Group of Pillsbury Madison & Sutro LLP

[57] ABSTRACT

A measuring electrode and a reference plate are formed on the front and rear surfaces, respectively, of the electrolytic plate. The vent plate is provided with a vent channel. The heater base comprises a heating element. The electrolytic plate is made of a green sheet of zirconium oxide consisting of 5 to 7 molar % $Y_2O_3$ and 0 to 5 parts by weight of aluminum oxide. The average particle diameter of the zirconium oxide powder is less than 2.0 μm. The green sheet of zirconium oxide has a thickness of 50 to 300 μm. The heater base is made of a green sheet of aluminum oxide consisting of aluminum oxide powder having an average particle diameter of less than 1.0 μm and 0 to 10 parts by weight of zirconium oxide or yttria-stabilized zirconium oxide. The green sheet of aluminum oxide is at least 4 times the thickness of the green sheet of zirconium oxide. To complete the oxygen sensor, these four components are sintered together at 1300° to 1600° C. to be integrated.

3 Claims, 3 Drawing Sheets

OXYGEN SENSOR

This is a division of application Ser. No. 08/226,551, filed Apr. 12, 1994 now U.S. Pat. No. 5,447,618.

BACKGROUND OF THE INVENTION

1. Field of the Invention

The present invention relates to an oxygen sensor for detecting the concentration of oxygen present in a gas such as exhaust gas from an internal combustion engine.

2. Description of the Related Art

An oxygen sensor is disclosed in Japanese Patent Publication Laid-Open No. 61-108957. FIG. 1 is originally used to explain the present invention, however since FIG. 1 is suitable to explain the related art, the related art is explained below based on FIG. 1. The oxygen sensor has a sensor portion for detecting the concentration of oxygen and a heater portion for heating the sensor portion to improve its ability to detect oxygen. An example of this oxygen sensor is provided with a sensor portion 10 and a heater portion 20.

The sensor portion 10 comprises a solid electrolytic plate 11 and a vent plate 16 provided with a vent channel 17. The vent plate 16 is mounted on the rear surface side of the electrolytic plate 11. A measuring electrode 12 is mounted on the front surface of the electrolytic plate 11, and a reference electrode 15 is mounted on the rear surface. The heater portion 20 includes an insulating layer 21 mounted on the rear surface of the vent plate 16, together with a heater base 22 having a heating element 25. The vent channel 17 in the vent plate 16 serves to force a reference gas such as air toward the reference electrode 15 on the rear side of the solid electrolytic plate 11.

The solid electrolytic plate 11, the vent plate 16, the insulating layer 21, and the heater base 22 are laminated and bonded integrally. The electrolytic plate 11, the vent plate 16, and the heater base 22 are made of zirconium oxide ($ZrO_2$). On the other hand, the insulating layer 21 is made of aluminum oxide ($Al_2O_3$) to provide electrical insulation between the vent plate 16 and the heating element 25 on the heater base 22.

The insulating layer 21 is made of aluminum oxide, while the vent plate 16 and the heater base 22 respectively located over and under the insulating layer 21 are made of zirconium oxide. Therefore, they are considered each sintered into bulk form (plate form) and then bonded together with an inorganic adhesive.

However, with an inorganic adhesive, there is a problem that the obtained adhesive strength is not sufficient to withstand stress produced by the difference between coefficients of thermal expansion in a cooling-heating cycle under environments in which the sensor is used. In consequence, the vent plate and the heater base will peel off from the adhesive layer.

Accordingly, a sandwich-type oxygen sensor as shown in FIG. 6 has been proposed. This sensor has a heating element 25 which has been previously surrounded by an insulating layer 21 of aluminum oxide. The heating element 25 is sandwiched between a vent plate 16 and a heater base 22. The insulating layer 21 is formed by printing aluminum oxide slurry around the heating element 25 such that the thickness of the aluminum oxide layer is less than 20 μm.

Where printing of the aluminum oxide slurry is utilized, it is difficult to form a compact insulating layer. Also, it is difficult to obtain sufficient electrical insulation at temperatures exceeding 700° C.

To circumvent these difficulties, there is a method of producing a separate heating element and bonding the bottom surface of a sensor portion opposite the electrode of the sensor portion having a hole for introducing the atmosphere with an inorganic adhesive. In this method, however, the adhesive is not reliable at high temperatures. Furthermore, the inorganic adhesive does not form a compact layer, thus deteriorating thermal conductivity.

SUMMARY OF THE INVENTION

It is an object of the present invention to provide an oxygen sensor including four members (i.e., a solid electrolytic plate, a vent plate, an insulating layer, and a heater base) firmly bonded integrally.

It is another object of the present invention to ensure sufficient ionic condition of the electrolytic plate required for an oxygen sensor and sufficient electrical insulation of the insulating layer.

The above objects are achieved in accordance with the constitution described below. The oxygen sensor is provided with a solid electrolytic plate consisting of powder of zirconium oxide having an average particle diameter of less than 2.0 μm, the electrolytic plate having a measuring electrode and a reference electrode formed respectively on two opposite surfaces of the electrolytic plate; a vent plate consisting of powder of aluminum oxide having an average particle diameter of less than 1.0 μm, the vent plate being mounted on a side of the reference electrode of the solid electrolytic plate, the vent plate being provided with a vent channel for guiding a reference gas to the reference electrode; and a heater base mounted on the vent plate. Therefore four members are firmly bonded integrally after sintering so that adhesive is reliable at high temperatures and the inorganic adhesive obtains excellent thermal conductivity by a compact adhesive.

DETAILED DESCRIPTION OF THE EMBODIMENTS

Figure 1:
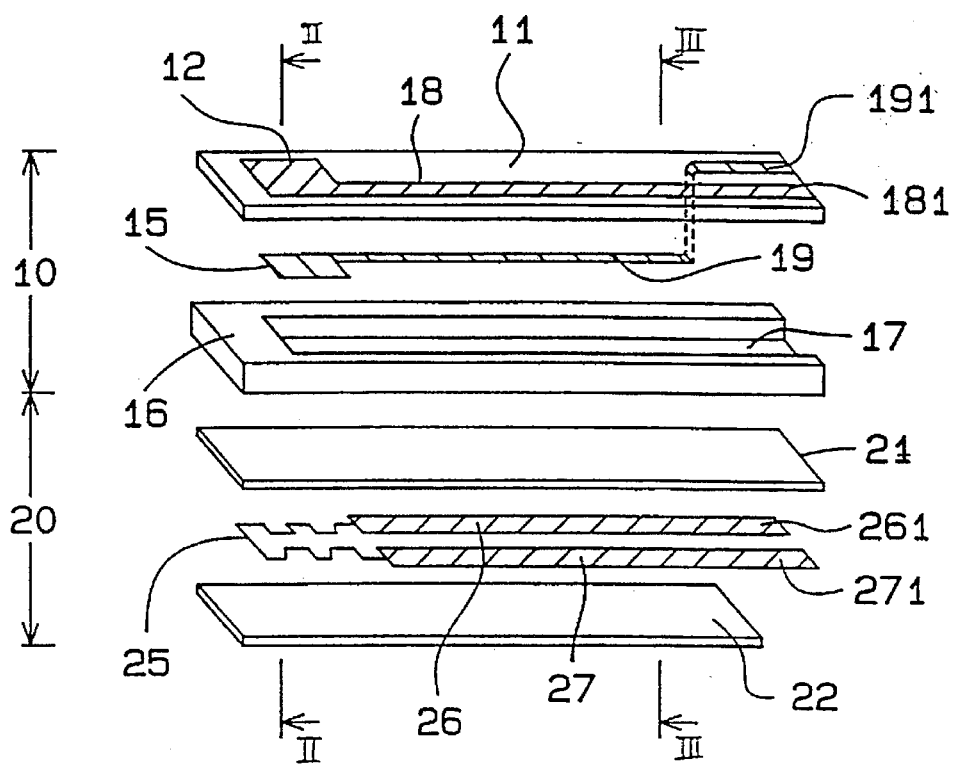
FIG. 1 is an exploded perspective view of an oxygen sensor according to Example 1 of the present invention.

As previously noted, the present invention is to provide an oxygen sensor including a solid electrolytic plate having a measuring electrode and a reference electrode on two opposite surfaces, respectively, of the electrolytic plate, a vent plate provided with a vent channel, an insulating layer, and a heater base having a heating element. The vent plate, the insulating layer, and the heater base are stacked on the rear surface of the electrolytic plate. These components are sintered integrally to form an integrated laminates. The electrolytic plate is made of a green sheet of zirconium oxide consisting of powder of zirconium oxide having an average particle diameter of less than 2.0 μm, 5 to 7 molar % yttria with respect to the powder of zirconium oxide, and 0 to 5 parts by weight of aluminum oxide. The thickness of the green sheet of zirconium oxide is 50 to 300 μm. The measuring electrode and the reference electrode are formed on the front and rear surfaces, respectively, of the green sheet of zirconium oxide.

The heater base is made of a green sheet of aluminum oxide consisting of powder of aluminum oxide having an average particle diameter of less than 1.0 μm and 0 to 10 parts by weight of zirconium oxide or yttria-partially stabilized zirconium oxide with respect to the powder of aluminum oxide. The green sheet of aluminum oxide is four or more times as thick as the green sheet of zirconium oxide. The heating element is formed on the front surface of the green sheet of aluminum oxide.

A green sheet for the vent plate, a green sheet of aluminum oxide for the insulating layer, and the abovedescribed green sheet of aluminum oxide are successively stacked on the rear surface of the green sheet of zirconium oxide. These sheets are heated and sintered together. Thus, the oxygen sensor is completed.

The present invention is characterized in that the solid electrolytic plate and the heater base are made of the above-described material and that the green sheet for the solid electrolytic plate, the green sheet for the vent plate, the green sheet for the insulating layer, and the green sheet for the heater base are stacked and sintered integrally.

In the green sheet of zirconium oxide for the solid electrolytic plate, the average particle diameter of the powder of zirconium oxide is less than 2.0 μm. If the average diameter is in excess of 2.0 μm, the powder is not sufficiently sintered. This makes it difficult to obtain a excellent quality solid electrolytic plate. The lower limit of the average particle diameter is 0.1 μm.

In another feature of the invention, 5 to 7 molar % yttria ($Y_2O_3$) and 0 to 5 parts by weight of aluminum oxide are added to 100 molar % of the above-described powder of zirconium oxide. If the yttria content is less than 5 molar % or greater than 7 molar %, the difference with the coefficient of thermal expansion of the aluminum oxide is large enough. As a result, cracks occurs.

If the aluminum oxide content is in excess of 5 parts by weight, the conductivity of oxygen ions deteriorates. The addition of aluminum oxide improves the fracture toughness of the solid electrolytic plate. However, where the solid electrolytic plate is not required to be very strong, aluminum oxide need not be added.

The thickness of the green sheet of zirconium oxide is 50 to 300 μm. If the thickness is less than 50 μm, then it is technically impossible to form a film of zirconium oxide and it causes problems in quality and treatment with ease. If the thickness exceeds 300 μm, cracks occurs in the oxygen sensor during sintering. A measuring electrode and a reference electrode are formed on the front and rear surfaces, respectively, of the green sheet of zirconium oxide by screen printing (see FIG. 1).

In the green sheet of aluminum oxide forming the heater base, the aluminum oxide powder has an average particle diameter of less than 1.0 μm. If the diameter is in excess of 1.0 μm, then the sheet is not sintered sufficiently. The lower limit of the average particle diameter is 0.05 μm to be sufficiently sintered.

The aluminum oxide powder (100 parts by weight) contains 0 to 10 parts by weight of zirconium oxide or a zirconium oxide additive consisting of $Y_2O_3$-stabilized zirconium oxide. If the zirconium oxide or zirconium oxide additive exceeds 10 parts by weight, a specific resistance (in other words, a volume resistivity) becomes small. As a result, where the sensor is used at high temperatures, a voltage due to a leakage current is superimposed on the sensor output signal. Where the zirconium oxide sheet thickness is relatively small, the zirconium oxide additive can be dispensed with.

The green sheet of aluminum oxide is at least four times the thickness of the green sheet of zirconium oxide. If the former green sheet is less than four times as thick as the latter green sheet, the solid electrolytic plate may crack during sintering of the oxygen sensor.

Preferably, the upper limit of the thickness of the green sheet of aluminum oxide is less than 8 times the thickness of the green sheet of zirconium oxide in order that heat is diffused through the sensor quickly.

The heating element is formed on the surface of the heater base by screen printing or a similar method. The vent plate and the insulating layer are made of unsintered sheets of the materials described below.

The above-described solid electrolytic plate, vent plate, insulating layer, and green sheet of aluminum oxide are stacked on top of each successively, and sintered integrally as shown in FIG. 1. Preferably, the temperature of the sintering is 1300° to 1600° C. to make an integrated laminates. If the temperature is below 1300° C., it is difficult to sinter integrally the green sheets of the four members. If the temperature is above 1600° C., excessive sintering is effected, causing movement of substances (aluminum oxide particles). This results in extraordinary growth of grains of aluminum oxide particles near stacked surface. In consequence, the bonding strength may be deteriorated.

Since the vent plate is bonded to the solid electrolytic plate, the vent plate is preferably made of zirconium oxide.

Because of electrical insulation, the insulating layer is made of aluminum oxide. In the present invention, the solid electrolytic plate and the heater base are constructed as described above and, therefore, the vent plate can be made of aluminum oxide in the same way as the insulating layer.

The green sheet of the vent plate preferably has a thickness of 150 to 2000 μm. The green sheet of the insulating layer preferably has a thickness of 50 to 2000 μm. Outside these ranges, it is difficult to yield the advantages of the invention.

In the method of producing an oxygen sensor, the green sheet of zirconium oxide is used for the solid electrolytic plate. The green sheet of aluminum oxide is used for the heater base. Green sheets of the vent plate and the insulating layer, respectively, are sandwiched between the green sheet of zirconium oxide and the green sheet of aluminum oxide. These sheets are sintered integrally to make an integrated laminates.

As a result, these four members are firmly bonded together. The solid electrolytic plate is produced from the green sheet of zirconium oxide, and the heater base is fabricated from the green sheet of aluminum oxide, both formed under the above conditions. Consequently, during sintering, great thermal stress is not produced. Also, neither the solid electrolytic plate nor the green sheet of aluminum oxide cracks.

Since the solid electrolytic plate is made of the aforementioned material, ionic conduction, which the oxygen sensor is intrinsically required to exhibit, is sufficiently secured.

The insulating layer is made of aluminum oxide which has excellent electrical insulating property.

Therefore, in the present invention, ionic conduction of the solid electrolytic plate and electrical insulation of the insulating layer, which the oxygen sensor must provide, can both be acquired. In consequence, an oxygen sensor including four members firmly bonded together is provided.

Other objects and features of the invention will become apparent in the course of the description thereof, which follows.

EXAMPLE 1

Figure 2:
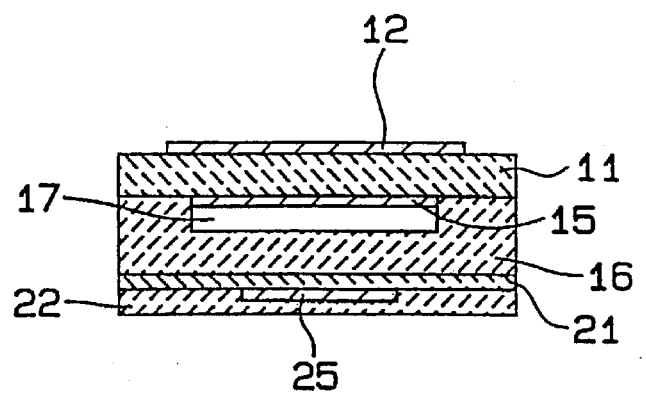
FIG. 2 is a cross-sectional view taken along line II—II of FIG. 1.
Figure 3:
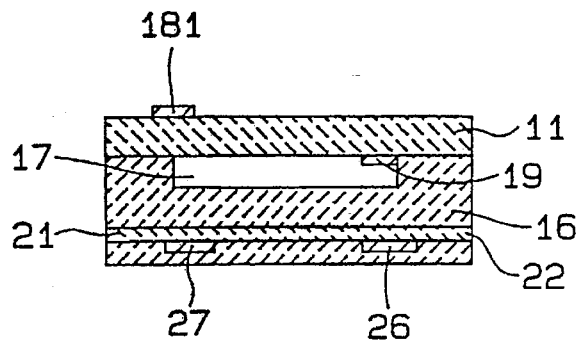
FIG. 3 is a cross-sectional view taken along line III—III of FIG. 1.

A method of producing an oxygen sensor according to the present example of the invention is now described by referring to FIGS. 1–3. This oxygen sensor includes a solid electrolytic plate 11, a vent plate 16, an insulating layer 21, and a heater base 22. A measuring electrode 12 is mounted on the front surface of the electrolytic plate 11. A reference electrode 15 is mounted on the rear surface of the electrolytic plate 11. The vent plate 16, the insulating layer 21, and the heater base 22 equipped with a heating element 25 are successively stacked on the rear surface of the electrolytic plate 11. These components are joined integrally by sintering them.

The solid electrolytic plate 11 and the vent plate 16 together form a sensor portion 10, while the insulating layer 21 and the heater base 22 together form a heater portion 20. The measuring electrode 12 and the reference electrode 15 mounted on the electrolytic plate 11 are respectively provided with leads 18 and 19, which are respectively provided with terminals 181 and 191. The measuring electrode 12, the reference electrode 15, and the leads 18 and 19 are made of a metal paste, such as platinum paste, by screen printing.

The vent plate 16 has a concave in cross section and is provided with a vent channel 17 for communication with the outside air. The reference electrode 15 of the electrolytic plate 11 is exposed to the vent channel 17, so that the reference electrode 15 is exposed to the outside air.

The insulating layer 21 is shaped like a flat sheet. The heating element 25 is formed on the top surface of the heater base 22. Leads 26 and 27, respectively having terminals 261 and 271, are connected with the heating element 25. The heating element 25 and the leads 26 and 27 are made of a metal paste, such as platinum paste, by screen printing.

The above-described oxygen sensor is produced by stacking a green sheet of zirconium oxide for the solid electrolytic plate, a green sheet for the vent plate, a green sheet for the insulating layer, and a green sheet of aluminum oxide for the heater base, and then sintering them.

EXAMPLE 2

The present example is a specific method of production of the oxygen sensor of Example 1. First, a green sheet of zirconium oxide for the solid electrolytic plate 11 was produced in the manner described below. A ceramic mixture consisting of 100 parts by weight of $Y_2O_3$-partially stabilized zirconium oxide, 1 part by weight of α-aluminum oxide, 5 parts by weight of polyvinyl butyral (PVB), 10 parts by weight of dibutyl phthalate (DBP), 10 parts by weight of ethanol, and 10 parts by weight of toluene was prepared. The partially stabilized zirconium oxide consisted of 6 molar % $Y_2O_3$ and 94 molar % zirconium oxide and had an average particle diameter of 0.5 μm.

Then, the mixture was mixed up in a ball mill, resulting in slurry. The slurry was shaped with a doctor resulting in slurry. The slurry was shaped with a doctor blade in such a way that the thickness obtained after drying would be 0.2 mm. This material was cut into a rectangle measuring 5 mm×70 mm. Subsequently, a hole extending through the rectangular material was formed in this material to permit a signal from the measuring electrode to be supplied close to the signal output portion of the reference electrode.

Then, the measuring electrode 12, the reference electrode 15, and their leads 18 and 19 were formed out of platinum paste by screen printing, thus forming a green sheet of zirconium oxide. This platinum paste contained 10 parts by weight of the same material as the slurry for the solid electrolytic plate.

Thereafter, a green sheet of aluminum oxide for the heater base 22 was produced in the following manner. A ceramic mixture consisting of 98 parts by weight of α-aluminum oxide having an average particle diameter of 0.3 μm, 3 parts by weight of partially stabilized zirconium oxide, 10 parts by weight of polyvinyl butyral (PVB), 10 parts by weight of dibutyl phthalate (DBP), 30 parts by weight of ethanol, and 30 parts by weight of toluene was prepared. The partially stabilized zirconium oxide contained 6 mole $Y_2O_3$.

Then, the mixture was mixed in a ball mill, resulting in slurry. The slurry was shaped with a doctor blade in such a way that the thickness obtained after drying would be 1.0 mm, which is 5 times the thickness of the green sheet of zirconium oxide. A dried material was obtained.

This material was cut into a rectangle measuring 5 mm×70 mm. Subsequently, a hole extending through the rectangular material was formed in this material. Thereafter, the heating element 25 and the leads 26 and 27 were formed out of platinum paste by screen printing, thus resulting in a green sheet of aluminum oxide. The platinum paste contained 10 parts by weight of the same material as the slurry for the heater base.

A green sheet for the vent plate 16 was formed out of aluminum oxide with a doctor blade in the same way as the above-described green sheet of zirconium oxide. The sheet of aluminum oxide was cut into a shape whose size was 5 mm×70 mm. The thickness thereof was 1.0 mm. The vent channel 17 measured 2 mm×67 mm and was 1.0 mm deep.

Similarly, an unsintered sheet of aluminum oxide for the insulating layer 21 was shaped into a flat sheet. This sheet was cut into a size measuring 5 mm×70 mm. The thickness was 1.0 mm.

The green sheets obtained as described above were stacked on top of each other in the same way as in Example 1 shown in FIG. 1 and pressed together. As a result, a laminate was derived.

Then, the laminate was sintered at 1300°–1600° C. In this way, an oxygen sensor was produced. No cracks were observed in the oxygen sensor. The insulating layer showed sufficient electrical insulation at temperatures of 800° to 900° C.

The laminate was produced by pressing the sheets together. Further a paste or adhesive sheets which contain powdered ceramic and an organic binder and show pressure-sensitive adhesiveness at room temperature may be sandwiched between the four sheets.

EXAMPLE 3

Figure 4:
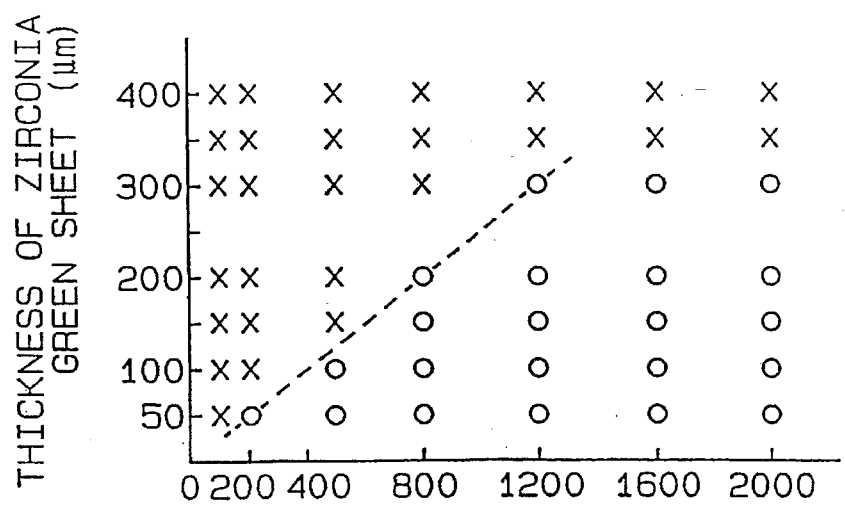
FIG. 4 is a diagram illustrating the relation of the thickness of a zirconium oxide green sheet to the thickness of an aluminum oxide green sheet in Example 3.

In the present example, green sheets of zirconium oxide having various thicknesses and green sheets of aluminum oxide having various thicknesses were prepared, and laminates was produced from them. The laminates were sintered to obtain oxygen sensors. These sensors were tested for cracks. Other conditions such as the compositions of the green sheets of zirconium oxide, the compositions of the green sheets of aluminum oxide, the vent plate, and the insulating layer were the same as those for Example 2. The above-described thicknesses and the results of tests are shown in FIG. 4. The crack tests included dyeing tests and airtightness tests. Oxygen sensors having no cracks are indicated by O in FIG. 4, while oxygen sensors having cracks are indicated by x. As can be seen from FIG. 4, where the green sheet of aluminum oxide of a laminate was at least four times the thickness of the green sheet of zirconium oxide of the laminate, no cracks occurred (indicated by O). Conversely, where the green sheet of aluminum oxide was less than four times the thickness of the green sheet of zirconium oxide, cracks occurred (indicated by x).

It can also be seen from FIG. 4 that where the thickness of the green sheet of zirconium oxide exceeds 300 μm, cracks are formed. Therefore, the thickness of the green sheet of zirconium oxide should be less than 300 μm.

It is generally considered that cracks are caused by a difference in the coefficient of thermal expansion, however it is also estimated from the results of the tests that the aforementioned compositions and shapes, etc caused the cracks.

EXAMPLE 4

The present example is similar to Example 2 except that green sheets of zirconium oxide were formed with various ratios of yttria ($Y_2O_3$) content to the zirconium oxide content of the solid electrolytic plate. Produced oxygen sensors were tested for cracks in the same way as in Example 3. The results are shown in Table 1 next.

TABLE 1

| $Y_2O_3$ content (molar %) | Test result |
| --- | --- |
| 3 | x |
| 4 | x |
| 5 | O |
| 6 | O |
| 7 | O |
| 8 | x |
| 9 | x |
| 10 | x |

When green sheets of zirconium oxide are formed, yttria is added to zirconium oxide. As can be seen from Table 1, the ratio of the yttria to the zirconium oxide is required to add within the range of from 5 to 7 molar %. Outside this range, the difference in coefficient of thermal expansion between the zirconium oxide and aluminum oxide (having a coefficient of thermal expansion of about $8.2 \times 10^{-6}$ cm/cm/°C.) is large during sintering and cooling processes. The strength thereof is not sufficient to withstand the produced stress and hence cracks occurs.

EXAMPLE 5

The present example is similar to Example 2, except that the amount of zirconium oxide added to aluminum oxide was changed to various values when the green sheet of aluminum oxide was formed. The resulting aluminum oxide sheets were sintered. A specific resistances of the formed heater bases were measured.

The specific resistances of the obtained heater bases at 1000° C. were measured. The relation of the specific resistance ($\rho$; M $\Omega$cm) of each heater base to the amount (parts by weight, or weight percentage) of zirconium oxide added to 100 parts by weight of aluminum oxide is shown in FIG. 5.

Figure 5:
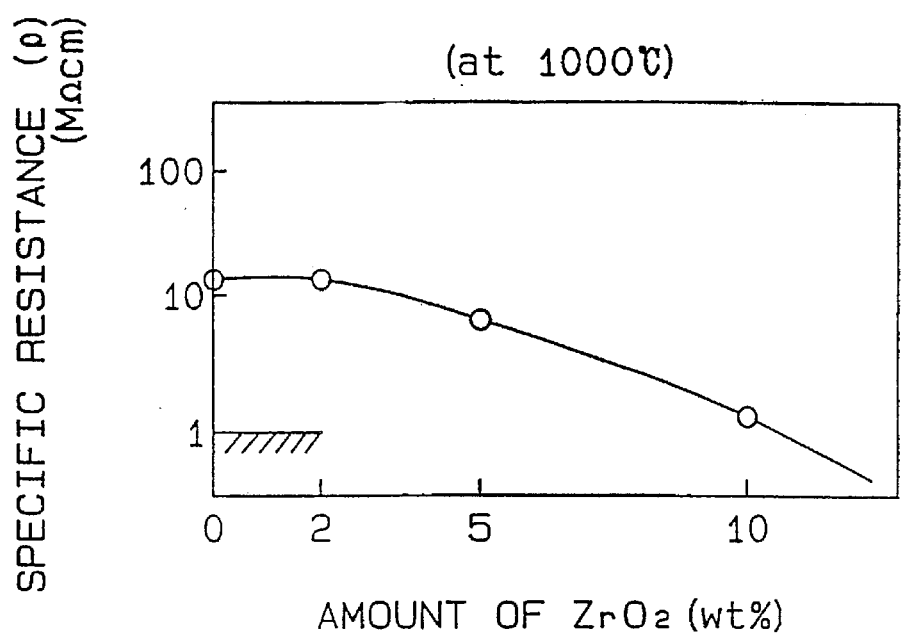
FIG. 5 is a diagram showing the relation of the specific resistance of the heater base of Example 5 of the invention to the amount of zirconium oxide contained in the heater base.
Figure 6:
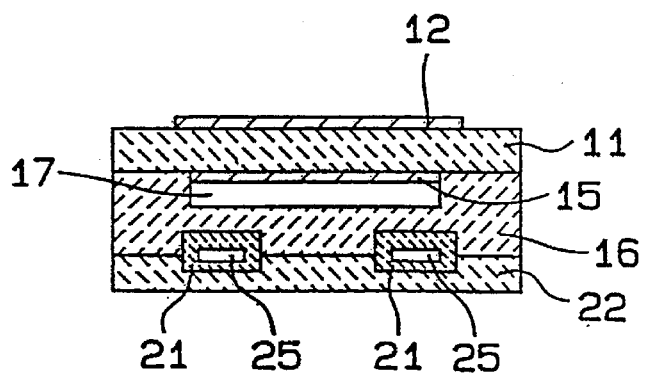
FIG. 6 is a cross-sectional view of a conventional oxygen sensor.

As can be seen from FIG. 5, where the zirconium oxide content exceeds 10%, the specific resistance (measured according to JIS (Japanese Industrial Standard), C 2141) does not reach 1M $\Omega$cm. As described previously, where zirconium oxide is added to aluminum oxide, the strength is improved. However, the above-described relation dictates that the amount of zirconium oxide added shall be less than 10 weight percent.

What is claimed is:

1. A method for producing an oxygen sensor for detecting an oxygen concentration in a gas comprising the steps of:

providing a solid electrolytic plate made of an unsintered sheet and having two surfaces, said solid electrolytic plate consisting of a powder of zirconium oxide having an average particle diameter ranging from 0.1 to 2.0 μm, said solid electrolytic plate containing 5 to 7 molar % yttria with respect to said powder of zirconium oxide, and said solid electrolytic plate containing greater than or equal to 0 and less than or equal to 5 parts by weight of aluminum oxide with respect to said powder, a thickness of said solid electrolytic plate being 50–300 μm;

forming a measuring electrode on one of said two surfaces of said solid electrolytic plate, said measuring electrode being exposed to a gas to be measured;

providing a reference electrode on another of said two surfaces of said solid electrolytic plate, said reference electrode being exposed to a reference gas;

laminating a vent plate made of an unsintered alumina sheet having two surfaces and being provided with a vent channel for guiding said reference gas to said reference electrode on said another of said two surfaces of said solid electrolytic plate, said unsintered alumina sheet consisting of a powder of aluminum oxide having an average particle diameter ranging from 0.1 to 1.0 μm, said unsintered alumina sheet containing greater than or equal to 0 and less than or equal to 10 parts by weight of one of zirconium oxide and yttria-partially stabilized zirconium oxide with respect to said powder of aluminum oxide contained in said alumina sheet, said alumina sheet being at least 4 times as thick as said electrolytic plate; and sintering said unsintered electrolytic plate and said unsintered alumina sheet to be integral.

2. The method for producing an oxygen sensor according to claim 1, comprising the additional step of providing a heating element at a surface side which is opposite to the surface side of said unsintered alumina sheet facing said unsintered electrolytic plate.

3. The method for producing an oxygen sensor according to claim 1, comprising the additional steps of:

providing a heater base;

providing an unsintered insulation sheet comprising alumina; and laminating said heater base, said unsintered insulation sheet, and said unsintered alumina sheet, on said another of said two surfaces of said electrolytic plate.

* * * * *